United States Patent
Krioutchkov et al.

(10) Patent No.: US 10,371,653 B2
(45) Date of Patent: Aug. 6, 2019

(54) MULTI-PHASE METERING DEVICE FOR OILFIELD APPLICATIONS

(71) Applicant: PERM Instruments Inc., Calgary (CA)

(72) Inventors: Serguei I. Krioutchkov, Calgary (CA); Apostolos Kantzas, Calgary (CA); Zheng Yin Wang, Calgary (CA)

(73) Assignee: PERM Instruments Inc., Calgary (CA)

( * ) Notice: Subject to any disclaimer, the term of this patent is extended or adjusted under 35 U.S.C. 154(b) by 890 days.

(21) Appl. No.: 14/925,509

(22) Filed: Oct. 28, 2015

(65) Prior Publication Data

US 2016/0047762 A1   Feb. 18, 2016

Related U.S. Application Data

(60) Continuation-in-part of application No. 14/083,308, filed on Nov. 18, 2013, now Pat. No. 9,804,108, which is a division of application No. 13/192,389, filed on Jul. 27, 2011, now Pat. No. 8,659,293.

(51) Int. Cl.
*G01N 24/08* (2006.01)
*G01V 3/32* (2006.01)
*G01R 33/34* (2006.01)

(52) U.S. Cl.
CPC ......... *G01N 24/081* (2013.01); *G01N 24/082* (2013.01); *G01V 3/32* (2013.01); *G01R 33/34053* (2013.01)

(58) Field of Classification Search
CPC ...... G01N 24/081; G01N 24/082; G01V 3/32; G01R 33/34053
See application file for complete search history.

(56) References Cited

U.S. PATENT DOCUMENTS

| | | | |
|---|---|---|---|
| 4,350,955 A | 9/1982 | Jackson et al. | |
| 5,023,551 A * | 6/1991 | Kleinberg | G01N 24/081 |
| | | | 324/303 |
| 5,602,477 A | 2/1997 | McCarthy et al. | |
| 5,680,043 A * | 10/1997 | Hurlimann | G01N 24/081 |
| | | | 324/303 |
| 5,990,417 A | 11/1999 | Senda et al. | |
| 6,157,276 A | 12/2000 | Hedeen et al. | |
| 6,346,813 B1 | 2/2002 | Kleinberg | |
| 6,605,943 B1 * | 8/2003 | Clark | G01R 33/50 |
| | | | 324/309 |
| 6,794,864 B2 | 9/2004 | Mirotchnik et al. | |
| 6,825,657 B2 | 11/2004 | Kleinberg et al. | |
| 6,844,492 B1 | 1/2005 | Wang et al. | |
| 6,846,985 B2 | 1/2005 | Wang et al. | |
| 6,952,096 B2 | 10/2005 | Freedman | |
| 7,053,611 B2 | 5/2006 | Freedman | |

(Continued)

FOREIGN PATENT DOCUMENTS

WO   2010077649 A2   7/2010

*Primary Examiner* — Dixomara Vargas
(74) *Attorney, Agent, or Firm* — Whitmyer IP Group LLC (57) ABSTRACT

This application is related to a system and methods for sampling fluids and gases using nuclear magnetic resonance (NMR) technology. Specifically the system is related to an improved metallic pipe design for use at oil and gas well heads that includes integral coils for transmitting an NMR pulse sequence and detecting NMR signals and can be used as a component of an NMR instrument. The methods are related to obtaining and analyzing NMR spectra in stationary and flowing states.

17 Claims, 8 Drawing Sheets

(56) References Cited

U.S. PATENT DOCUMENTS

| | | |
|---|---|---|
| 7,091,719 B2 | 8/2006 | Freedman |
| 7,463,027 B2 | 12/2008 | Prammer et al. |
| 7,643,027 B2 | 1/2010 | Rothstein et al. |
| 7,667,462 B2 | 2/2010 | Song et al. |
| 7,683,613 B2 | 3/2010 | Freedman et al. |
| 7,777,489 B2 | 8/2010 | Kawamoto |
| 7,940,043 B2 * | 5/2011 | Gao ................. G01N 24/08 324/303 |
| 8,411,394 B2 | 4/2013 | Sato |
| 8,487,727 B2 | 7/2013 | Wu et al. |
| 8,659,293 B2 * | 2/2014 | Krioutchkov ........ G01N 24/081 324/307 |
| 9,551,769 B2 | 1/2017 | Fordham et al. |
| 9,678,185 B2 * | 6/2017 | Corkery ................. G01N 24/08 |
| 9,804,108 B2 * | 10/2017 | Krioutchkov ........ G01N 24/081 |
| 9,864,031 B2 * | 1/2018 | Reiderman ........ G01N 24/081 |
| 2004/0254419 A1 | 12/2004 | Wang et al. |
| 2005/0025797 A1 | 2/2005 | Wang et al. |
| 2005/0079132 A1 | 4/2005 | Wang et al. |
| 2007/0222444 A1 | 9/2007 | Reiderman |
| 2009/0072825 A1 | 3/2009 | Prammer et al. |
| 2009/0128144 A1 | 5/2009 | Freedman et al. |
| 2010/0001730 A1 | 1/2010 | Stephenson et al. |
| 2012/0092008 A1 | 4/2012 | Krioutchkov et al. |
| 2016/0018493 A1 * | 1/2016 | Reiderman ........ G01N 24/081 324/309 |
| 2016/0047762 A1 | 2/2016 | Krioutchkov et al. |
| 2017/0212063 A1 * | 7/2017 | Kantzas ............... G01N 24/081 |

* cited by examiner

MULTI-PHASE METERING DEVICE FOR OILFIELD APPLICATIONS

FIELD OF THE INVENTION

This application is related to a system and methods for sampling fluids and gases using nuclear magnetic resonance (NMR) technology. Specifically the system is related to a robust field oriented NMR system and an improved metallic pipe design for use at oil and gas well heads that includes integral coils for transmitting an NMR pulse sequence and detecting NMR signals and can be used as a component of an NMR instrument. The methods are related to obtaining and analyzing NMR spectra in stationary and flowing states.

BACKGROUND OF THE INVENTION

In the oil and gas industry, production well-testing at oil and gas wellheads is performed to quantify the amount of water, oil and gas produced from an individual well. This information is important as it allows the parameters of oil production to be adjusted in order to maximize the efficiency of the production well. Conventional well testing technologies, such as Test Separators and Dean Stark extraction, generally involve the use of large scale and expensive equipment that is time-consuming to use and that, as a result of the complexity of the equipment, often leads to delays during well production. Alternative metering technologies, such as Nuclear Magnetic Resonance (NMR), Microwaves, and Gamma Ray based meters, are becoming increasingly available and generally have the potential to offer savings in terms of time, space, and cost in comparison to conventional well testing technologies. In addition, these alternative metering technologies typically have the capability to be more reliable and accurate compared to conventional well testing technologies. A magnetic resonance apparatus is described in U.S. Pat. No. 4,350,955.

In general, conventional pipes used to convey hydrocarbon fluids from wells have a metallic component to them. Metallic pipes are known to create problems for certain alternative metering technologies, such as nuclear magnetic resonance (NMR) meters. NMR meters function by applying an external static magnetic and a pulsating electromagnetic field to a sample to determine the components of the sample in terms of water, oil and gas content. Such systems are described in US Patent Publication No. 2009/0128144; US Patent Publication No. 2009/0072825; U.S. Pat. Nos. 6,346,813; 7,463,027; US Patent Publication No. 2010/0001730; and U.S. Pat. No. 6,825,657. As NMR meters use magnetic fields, metallic materials located near NMR meters will serve as transmitters and undermine the accuracy and sensitivity of the NMR meter. As such, there is generally a need for systems that mitigate these problems, and more specifically there has been a need for improved pipe designs that can be used with an NMR metering tool to increase the accuracy and sensitivity of an NMR meter in the field.

In addition, the oil and gas industry generally operates in a high pressure, temperature and corrosive environment where process fluids are typically comprised of hydrocarbons, hydrogen sulfide, water, steam, carbon dioxide and inert substances such as nitrogen gas and sand particles. As is known, high temperatures and pressures are routinely encountered in a production well, with temperatures reaching 533 K (260° C.; 500° F.) and pressures reaching 4136 kPa (600 Psi). Thus, in the context of alternate metering technologies, including NMR equipment, there continues to be a need for effective apparatus for containing a fluid sample at well head that can withstand the corrosive ent of oil and gas wells as well as the high temperatures and pressures of oil and gas wells while also enabling effective alternative metering technologies.

A review of the prior art indicates that such systems and particularly NMR systems have not been developed. For example, U.S. Pat. Nos. 7,053,611; 7,091,719; 6,952,096 and US Patent Publication No. 2007/0222444 describe methods for determining fluid properties in formations using NMR instruments.

As a result, there continues to be a need for well-testing equipment and methodologies, particularly for NMR instruments, that improve the effectiveness of NMR measurements in both stationary and moving fluids and can be performed in a short period of time in the field.

SUMMARY OF THE INVENTION

According to a first aspect, there is provided a method of measuring the relative quantities of fast-relaxing and slow-relaxing components in a sample flow using nuclear magnetic resonance (NMR) relaxometry, comprising the steps of:

flowing a sample comprising at least two components through the pipe, the at least two components comprising a fast-relaxing component and a slow-relaxing component;

measuring a relaxation curve corresponding to at least one fast-relaxing component as the sample flows through the pipe;

calculating a proportion of fast-relaxing component in the flowing sample based on relaxation spectra obtained from the measured relaxation curve; and calculating a proportion of a slow-relaxing component in the flowing sample based on the calculated proportion of fast-relaxing component.

It will be appreciated that the fast-relaxing components may relax more rapidly than the slow-relaxing components. The relaxation rate may be considered to relate to the spin-spin or transverse relaxation time. The relaxation curve may be measured using an NMR coil. The NMR coil may be aligned with the axis of the pipe. A pipe may be considered to be a channel configured to transmit fluid from one end to another end.

The calculating steps may be performed by a processor in conjunction with a memory (e.g. non-transitory memory such as RAM or a CD) having suitable computer program code, the computer program code being configured to be executed by the processor.

The at least one fast-relaxing component may comprise oil.

The at least one slow-relaxing component may comprise water.

The method may comprise: calibrating the NMR pipe with a stationary sample comprising a known proportion of a fast-relaxing component. The method may comprise calculating the equivalent signal for a pure sample of the fast-relaxing component based on a measured signal corresponding to the known proportion of a fast-relaxing component (e.g. scaling the measured signal based on the known proportion).

The calibration step may comprise calibrating the NMR pipe with a pure sample of the fast-relaxing component.

The fluid may be flowing at a speed that allows collection of a fast-relaxing component relaxation signal without counting for a slow-relaxing component relaxation signal.

The method may comprise repeating one or more of the calibration steps over a selected temperature range. The method may comprise measuring the temperature of the flowing sample and adjusting the calculations and/or the flow rate accordingly.

The proportion of the slow-relaxing component, $S_{src}$, may be calculated as: $S_{src}=1-S_{frc}$, where $S_{frc}$ is the proportion of fast-relaxing component. For samples with N components, the proportion of the slowest-relaxing component, $S_N$, may be calculated as: $S_N=1-\Sigma_{i=1}^{N-1} S_i$, where $S_i$ is the proportion of fast-relaxing component, i.

The method may comprise creating the relaxation spectra for the sample using a standard NNLS (non-negative least-squares) algorithm.

The mixture may consist of two components.

The method may comprise:
measuring the sample flow rate; and
calculating a cut of a slow-relaxing component based on relaxation spectra obtained from the measured relaxation curves and on the measured flow speed.

The flow rate may be considered to be a measure of how quickly the sample is flowing through the pipe. The flow rate may correspond to a flow speed, the flow speed being the linear speed of the fluid through the pipe. The flow rate may correspond to the volumetric flow rate within the pipe. The flow speed may be calculated by dividing the volumetric flow rate by the cross-sectional area of the pipe.

The relaxation curve may be measured over a measurement period. The measurement period may correspond to the duration of time after the initial NMR signal is applied to the sample in which the response of the sample is measured. The measurement period may correspond to the sample response time which is used to calculate the proportion of fast-relaxing component. The measurement period may correspond to a time greater than the relaxation time range of the fast-relaxing component and slower than the relaxation time range of the slow-relaxation component.

According to a further aspect, there is provided an NMR apparatus for measuring the relative quantities of fast-relaxing and slow-relaxing components in a sample flow using nuclear magnetic resonance (NMR) relaxometry, the NMR apparatus comprising:
a pipe configured to receive a flowing sample comprising at least two components, the at least two components comprising a fast-relaxing component and a slow-relaxing component;
NMR components configured to measure a relaxation curve corresponding to at least one fast-relaxing component of the flowing sample; and
a processor configured to calculate a proportion of fast-relaxing component in the flowing sample based on relaxation spectra obtained from the measured relaxation curve; and to calculate a proportion of a slow-relaxing component in the flowing sample based on the calculated proportion of fast-relaxing component.

According to a further aspect, there is provided a method of measuring the relative quantities of components in a fluid using nuclear magnetic resonance (NMR) relaxometry in an NMR pressure tube or pipe, comprising the steps of:
calibrating the NMR pressure tube or pipe with a pure oil sample;
introducing at least a two-component mixture into the NMR pressure tube or pipe, wherein the mixture comprises oil and water;
measuring relaxation curves of a hydrogen signal; and
calculating water-cut based on relaxation spectra obtained from the measured relaxation curves.

According to a further aspect, there is provided an NMR apparatus for measuring the relative quantities of components in a fluid, the NMR apparatus comprising a electronic circuit having a processor and a NMR pressure tube, the NMR apparatus being configured to:
calibrate the NMR pressure tube or pipe with a pure oil sample;
introduce at least a two-component mixture into the NMR pressure tube or pipe, wherein the mixture comprises oil and water;
measure relaxation curves of a hydrogen signal; and
calculate water-cut based on relaxation spectra obtained from the measured relaxation curves.

In accordance with the present disclosure, there is provided a pipe system for enabling nuclear magnetic resonance (NMR) analysis of gas and/or liquids within the pipe system. The pipe system may comprise a pipe containing an NMR resonator coil. The pipe system may comprise: an inner layer defining an internal volume within the pipe system; an insulating layer in operative contact with the inner layer, the insulating layer containing and supporting an NMR resonator coil. a shielding layer in operative contact with the insulating layer; and an outer non-magnetic layer in operative contact with the shielding layer for operatively containing pressurized fluids within the inner layer.

In further embodiments, the outer non-magnetic layer is selected from any one of or a combination of titanium, stainless steel, beryllium, and copper. In a preferred embodiment, the outer non-magnetic layer is titanium.

In yet another embodiment, the ratio of the diameter of the NMR resonator coil and the diameter of the shielding layer ($D_R/D_{SL}$) is between 0.3 and 0.7.

In other embodiments, the shielding layer is selected from any one of or a combination of silver, copper, titanium and a super conductor. If the shielding layer is copper, it is preferred the ratio of the diameter of the NMR resonator coil and the diameter of the shielding layer ($D_R/D_{SL}$) is 0.5-0.6. If the shielding layer is titanium, it is preferred the ratio of the diameter of the NMR resonator coil and the diameter of the shielding layer ($D_R/D_{SL}$) is 0.3-0.4. The ratio of the diameter of the NMR resonator coil and the diameter of the shielding layer ($D_R/D_{SL}$) may be between 0.3 and 0.7.

In various embodiments, the insulating layer is a resin and/or a thermoplastic such as polyetheretherketone (PEEK).

In one embodiment, the resonator coil is copper. In another embodiment, the resonator coil is the same material as the shielding layer. In another embodiment, the insulating layer has a higher conductivity than the resonator coil.

In other embodiments, the inner layer is polyetheretherketone (PEEK) or Teflon® (polytetrafluoroethylene).

In another embodiment, the length of the resonator coil along the pipe is greater than twice the diameter of the resonator coil.

In one embodiment, the resonator coil comprises a plurality of coils connected in parallel.

In another aspect, the present disclosure provides a nuclear magnetic resonance system comprising: a low field (1-5 MHz) permanent magnet operatively configured to an NMR pipe system; a pulse signal creation circuit operatively connected to the resonator coil for generating radiofrequency (RF) pulsations to the resonator coil; a RF receiver circuit for receiving and filtering RF data from the pipe system for delivery to a data acquisition system; a transceiver switch circuit operatively connected to the pulse signal creation circuit and RF receiver circuit for operative switching between a signal creation and a signal listening mode; and an explosion proof container for operative containment of the magnet, pulse signal creation and RF receiver circuit and transceiver circuit. The system may also include an air purge cooling system for maintaining a positive pressure within the explosion proof container.

In yet another aspect, the present disclosure provides a method of measuring the relative quantity of a gas or liquid in a high temperature and pressure fluid using nuclear magnetic resonance (NMR) relaxometry in an NMR pressure tube, comprising the steps of: a) calibrating the NMR pressure tube with a pure water sample; b) calibrating the NMR pressure tube with a pure oil sample; c) repeating steps a) and b) over a selected temperature range; d) introducing at least a two-component mixture into the NMR pressure tube; e) measuring relaxation curves of a hydrogen signal; and f) calculating water-cut based on relaxation spectra obtained from relaxation curves of step e). The two-component mixture may be stationary or be flowing within the NMR pressure tube.

Oil may comprise aromatic and/or aliphatic hydrocarbons. Oil may comprise bitumen.

According to a further aspect, there is provided a pipe system for enabling nuclear magnetic resonance (NMR) analysis of gas and liquids within the pipe system comprising: an inner layer defining an internal volume within the pipe; a thermoplastic insulating layer in operative contact with the inner layer, the insulating layer containing and supporting an NMR resonator coil; a shielding layer selected from any one or a combination of silver, copper, titanium and a superconductor, in operative contact with the thermoplastic insulating layer; and an outer non-magnetic layer selected from any one of or a combination of titanium, stainless steel, beryllium and copper, in operative contact with the shielding layer for operatively containing pressurized fluids within the inner layer.

According to a further aspect, there is provided a pipe system for enabling nuclear magnetic resonance (NMR) analysis of gas and liquids within the pipe system comprising: an inner layer composed of polyetheretherketone (PEEK) defining an internal volume within the pipe; a thermoplastic insulating layer made of polyetheretherketone (PEEK) in operative contact with the inner layer, the insulating layer containing and supporting an NMR resonator coil made of copper; a shielding layer made of titanium, in operative contact with the insulating layer; and an outer non-magnetic layer made from titanium in operative contact with the shielding layer for operatively containing pressurized fluids within the inner layer.

Further Explanation of Terms $T_2$ is the spin-spin or transverse relaxation time. $T_2$ may be dependent on a number of parameters including: resonance frequency (field strength); temperature; mobility of the observed spin (microviscocity); and/or presence of large molecules, paramagnetic ions and molecules, or other outside interference.

In addition to rotation, the net magnetization starts to dephase because each of the spin packets making it up is experiencing a slightly different magnetic field and rotates at its own Larmor frequency. The longer the elapsed time, the greater the phase difference. Here the net magnetization vector is initially along the y-axis. For this and all dephasing examples think of this vector as the overlap of several thinner vectors from the individual spin packets.

The time constant which describes the return to equilibrium of the transverse magnetization, $M_{XY}$, is called the spin-spin relaxation time, $T_2$. The transverse magnetization, $M_{XY}$ varies with time, t, follows:

$$M_{XY}=M_{XY0}e^{-t/T_2},$$

where $M_{XY0}$ is the initial transverse magnetization. The net magnetization in the x-y plane goes to zero and then the longitudinal magnetization grows in until the magnetic field aligns with the z direction. Any transverse magnetization may behave the same way. The transverse component rotates about the direction of applied magnetization and dephases.

$T_2^*$ is the characteristic experimental relaxation decay time of transverse magnetization caused by a combination of spin-spin relaxation ($T_2$) and device parameters (e.g. magnetic field inhomogeneity). Magnetic field inhomogeneity may include static field non-uniformity (e.g. due to imperfections in the construction of the scanner magnet itself as well as from magnetic susceptibility effects in the sample). The combination of these two factors is what actually results in the experimental decay of transverse magnetization (which may also be an exponential decay). The relationship between the $T_2$ from molecular processes and that from apparatus in the magnetic field is as follows:

$$1/T_2^*=1/T_2+1/T_{2a},$$

where $T_{2a}$ is the characteristic instrument decay time. The sample decay constant may be considered to be $1/T_2$ and the apparatus decay constant may be considered to be $1/T_{2a}$. Therefore, analogous to the sample decay equation above, the experimental decay response, $M_{XY}^*$ may be of the form:

$$M_{XY}^*=M_{XY0}^*e^{-t/T^*2}$$

$T_E$ is the echo time. The echo Time ($T_E$) may be considered to be the time between the transverse pulse and the maximum of echo response. In some cases, the echo time may be considered to be the time between two successive echoes. Generally, the first refocusing pulse is applied at time $t=T_E/2$ after the transverse pulse.

$T_{2gm}$ is the geometric mean relaxation time or the weighted average of $T_2$ and is the mean of the T2 distribution. The mean is a logarithmic average, since the $T_2$ values in an NMR spectrum are plotted on a logarithmic scale. That is, $T_{2gm}$ is the geometric mean relaxation time. This mean is calculated by weighted averaging of $T_2$ logarithms and by exponentiation of the result. Since the $T_2$ values in an NMR spectrum are distributed over several orders of magnitude this mean may be more suitable for spectrum characterization than, for example, weighted arithmetic mean.

For a single exponentially decaying fluid such as water, the relaxation time of the fluid can be expressed as essentially a single value of $T_2$. For more complex systems such as oil or water in multiple pore sizes, the fluid relaxation time is better described by this mean value. In this manner, $T_{2gm}$ may be used to characterize the overall property of $T_2$ and is calculated using the equation:

$$T_{2gm} = \exp\left[\frac{\sum_i A_i \ln(T_{2i})}{\sum_i A_i}\right],$$

where $A_i$ is the amplitude value corresponding to a specific relaxation time $T_{2i}$. $T_{2gm}$ may be calculated for a sample and/or for one or more components of a sample (e.g. the oil component and/or the water component).

BRIEF DESCRIPTION OF THE DRAWINGS

The invention is described with reference to the accompanying figures in which.

DETAILED DESCRIPTION OF THE INVENTION

With reference to the figures, an NMR-compatible system 10 for use with an NMR instrument 12 and methods for determining the content of a fluid at oil and gas well heads using the NMR-compatible system and NMR instrument are described.

NMR-Compatible Apparatus

Figure 3:
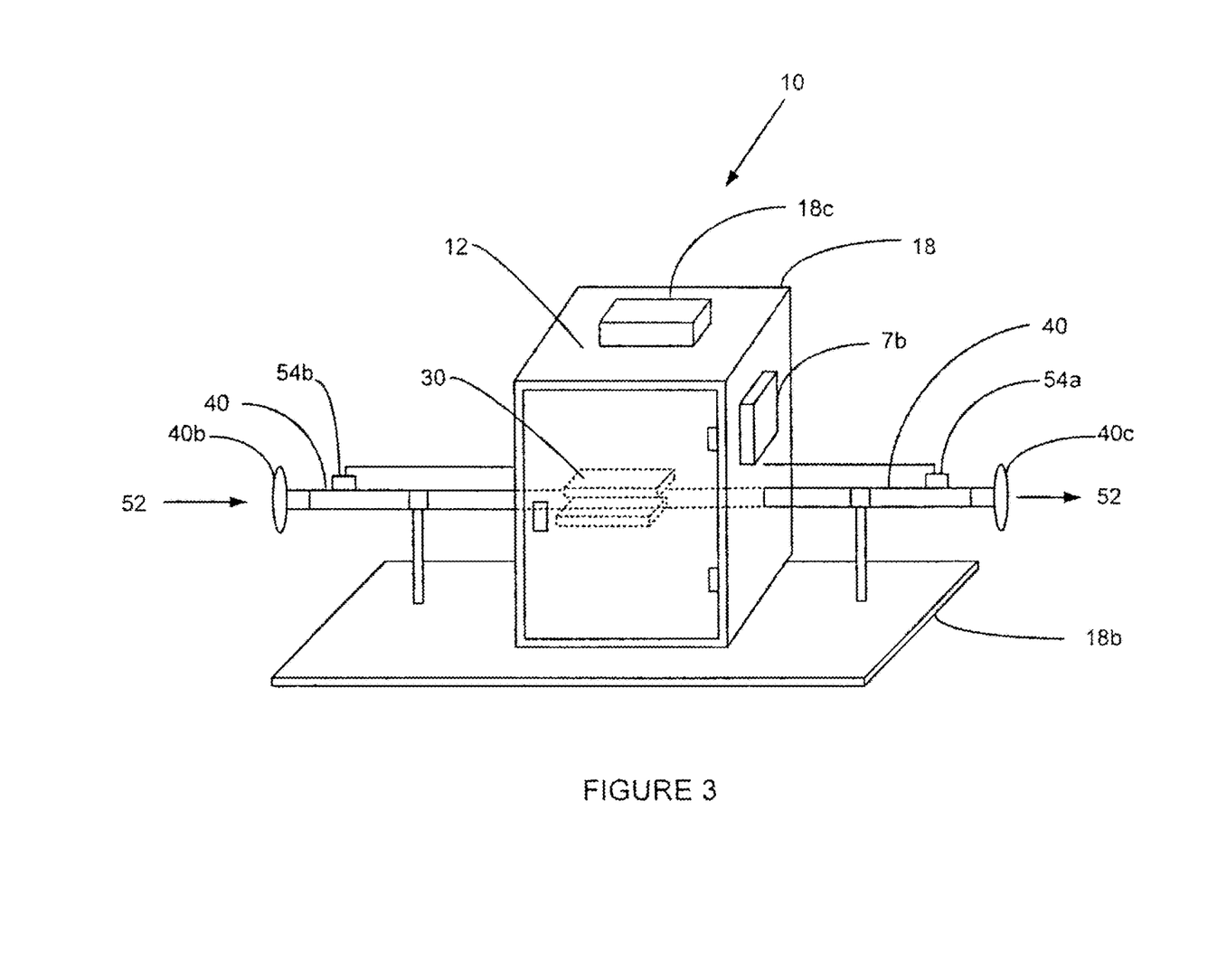
FIG. 3 is a front sectional view of an NMR apparatus in accordance with one embodiment.

As shown in FIG. 3, the NMR-compatible system 10 consists of an NMR pipe 40 that is connected to conventional well-head piping (not shown). The NMR pipe 40 has connection devices 40b, 40c at each end to secure the pipe to the conventional pipe. A portion of or all fluid from the conventional pipe is diverted through the NMR pipe 40 in a one-way direction, as shown in FIG. 3, wherein the fluid within the NMR pipe is subjected to NMR measurement by the NMR instrument 12 to determine the content of the fluid sample.

Figure 1:
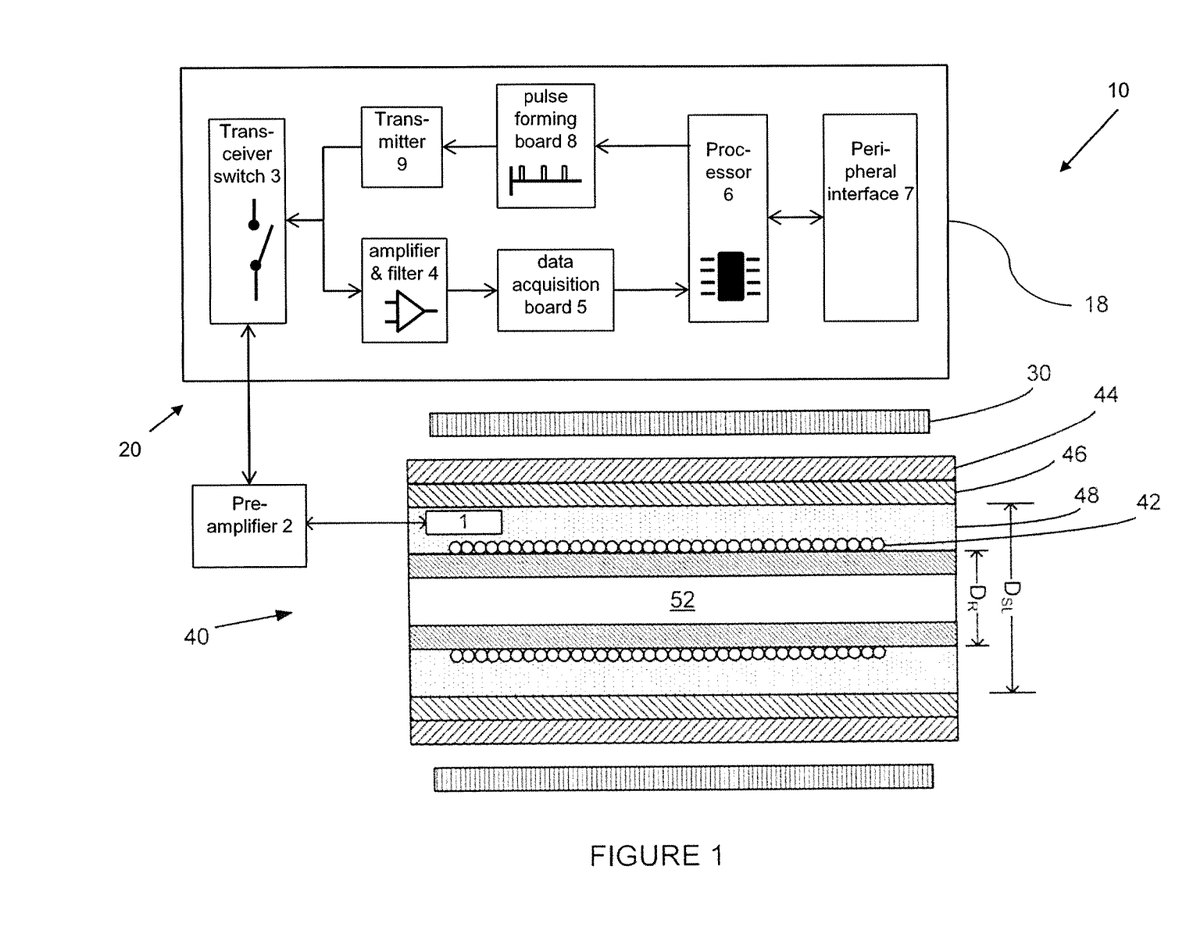
FIG. 1 is a schematic view of an NMR apparatus for use in an NMR instrument in accordance with one embodiment.
Figure 2:
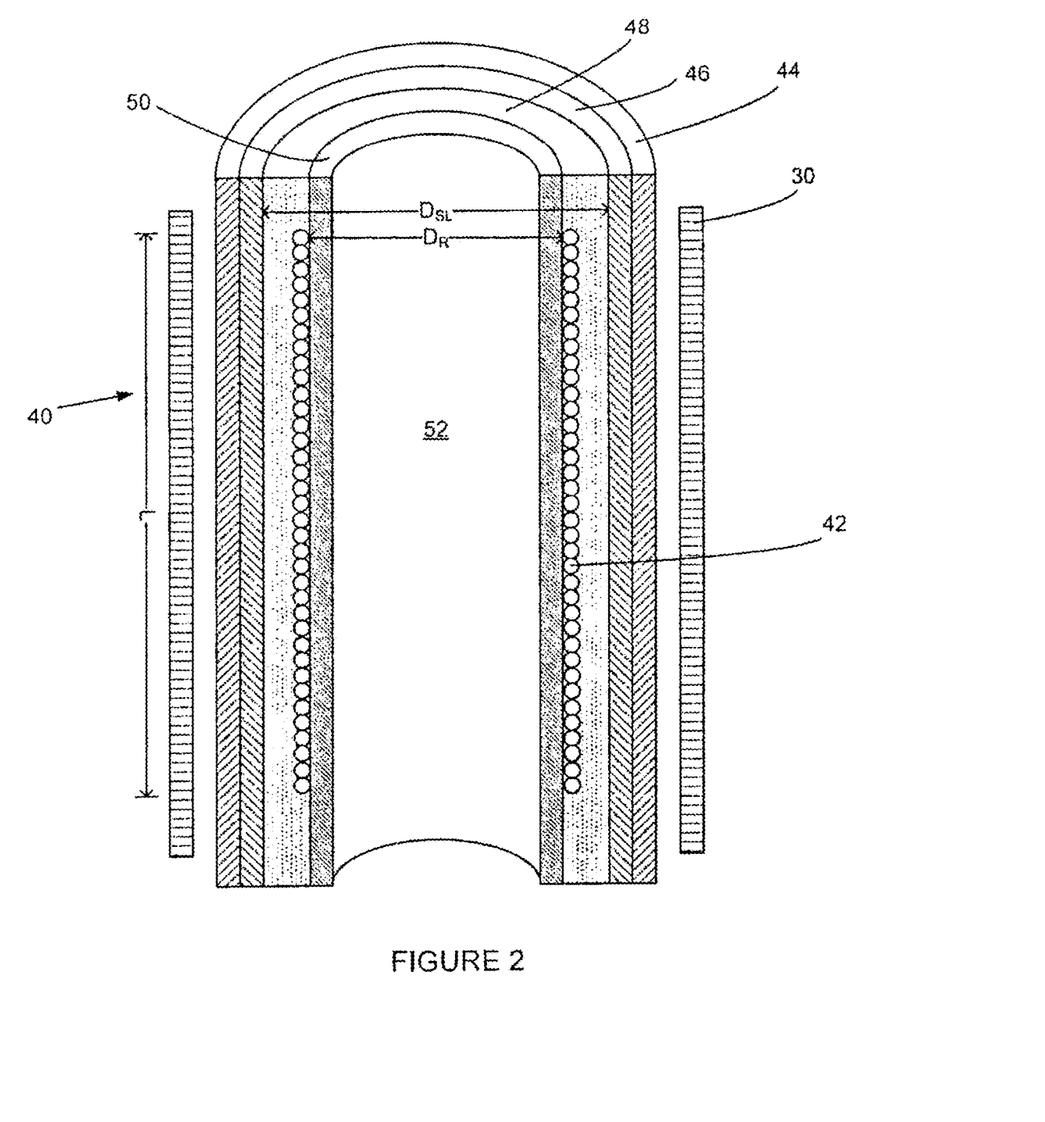
FIG. 2 is a cross-sectional view of an NMR compatible pipe in accordance with one embodiment.
Figure 2A:
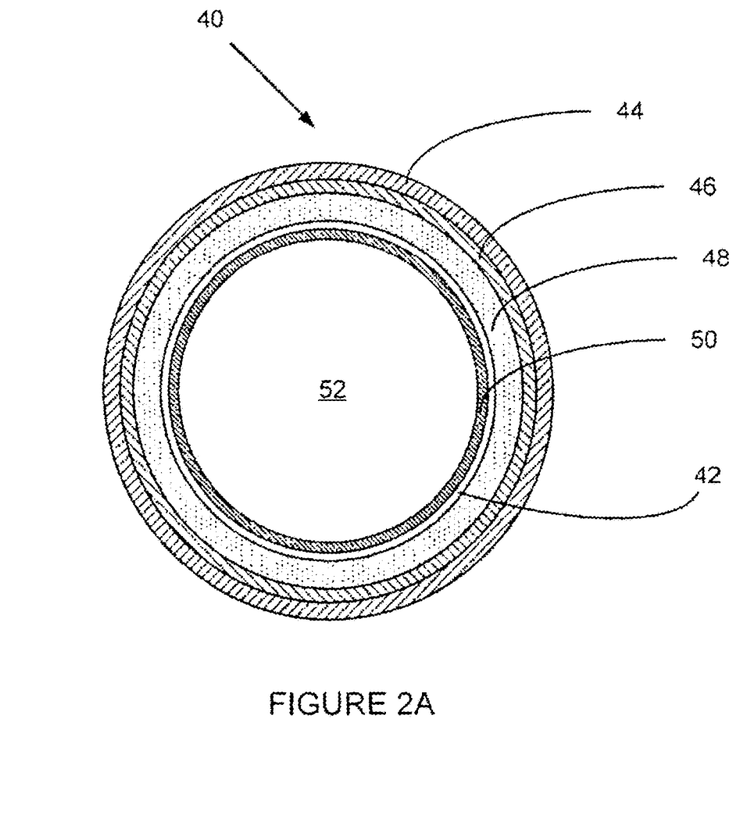
FIG. 2A is a schematic end view of an NMR pipe in accordance with one embodiment.

FIGS. 1, 2 and 2A illustrate the pipe 40 as having a resonator 42 located inside the NMR pipe for the transmission of a pulse sequence and NMR signal detection, and several layers including an outer layer 44, a shielding layer 46, a gap layer 48 and a core layer 50. An appropriate NMR magnet 30 surrounds the pipe 40 such as a permanent low field magnet (1-5 MHz).

As shown in FIGS. 1 and 3, to enable field-use and deployment, the apparatus 10 is secured to a skid 18b and further includes an electronic circuit 20 for generating and detecting the NMR signals. The electronic circuit preferably comprises a matching circuit 1, a preamplifier 2, a transceiver switch 3, an amplifier and filter 4, a data acquisition board 5, a computer/processor 6, a peripheral interface 7, a pulse forming board 8 and a transmitter 9. Preferably, various components of the electronic circuit 20 are enclosed in an explosion proof cabinet 18, shown in FIG. 1 and FIG. 3, in which an inside positive pressure is maintained preferably through the use of compressed air. A temperature control and purge unit 18c is located on the outside of the cabinet 18, along with a port 7b for the peripheral interface 7. First and second resistive thermal devices (RTDs) 54a, 54b are attached to the input and output ends of the pipe 40 to measure temperature.

As is known to those skilled in the art, the magnet 30 creates a strong, homogenous magnetic field that causes certain nuclei within the fluid sample 52 to line up within the magnetic field. The pulse forming board 8 provides pulsations of radiofrequency (RF) energy in a CPMG (Carr, Purcell, Meiboom and Gill) sequence that are transmitted to the resonator 42. The RF signal excites aligned molecules within the sample that then cause certain atomic nuclei to resonate. When the RF signal is turned off, the nuclei "relax" and produce a weak RF signal which induces a small current in the resonator coil that is received by the data acquisition board. The current is processed and analyzed by the processor to create NMR spectra for the sample using a standard NNLS (non-negative least-squares) algorithm. As atoms of different substances relax at different rates, it is possible to determine the relative amounts of particular atoms in the sample using NMR relaxometry analysis, of which methods are described below. In the preferred embodiment of the invention, hydrogen atoms are excited and hydrogen bearing molecules are detected.

Pipe Layers

The different layers of the pipe 40 are designed to maximize the signal-to-noise (SNR) ratio of the NMR instrument by maximizing the sample volume of the fluid 52 for a given diameter of pipe. In NMR, SNR is proportional to the square root of the quality factor (Q) of the resonator 42 and to the sample volume. It is preferable that the Q factor is optimized for SNR and for ringing time constant, which is proportional to Q. At some point of Q, ringing time (recovery time or dead time) is minimal in order to maximize SNR. As known to those skilled in the art, there are practical methods, such as active damping, that can be used to improve SNR while keeping recovery time minimal.

The non-magnetic outer layer 44 has mechanical characteristics designed to withstand the high temperatures and pressures that pipes used in oil and gas operations typically encounter. Suitable materials include stainless steel, beryllium, copper, and titanium. Preferably titanium (Grade 2 or Grade 5) is used, as a lesser thickness of titanium is required in comparison to beryllium, copper, and stainless steel to provide the necessary mechanical characteristics. The smaller wall thickness translates into a larger available volume inside the pipe for the sample fluid, which effectively increases the SNR of the instrument.

Located interior to the outer layer 44 is the shielding layer 46 that is designed to shield the resonator 42 from outside noise. The shielding layer is preferably made from the same material as the resonator 42, such as copper. Alternatively the shielding layer is manufactured from a non-magnetic material with a higher conductivity than the material of the resonator in order to maximize the Q factor of resonator 42. Table 1 below illustrates the ratio of the resonator diameter ($D_r$) to shielding layer diameter ($D_{sl}$) to maximize the Q factor of the resonator for a given shielding layer material.

TABLE 1

Ratio Of Resonator Coil Diameter ($D_r$) To Shielding Layer Diameter ($D_{sl}$) To Maximize The Q Factor For A Given Shielding Layer Material

| Shielding Layer Material | Relative high frequency effective resistance to copper | Best ratio of $D_r/D_{sl}$ to maximize Q factor of resonator |
|---|---|---|
| Super Conductor | 0 | 0.659 |
| Silver | 0.98 | 0.552 |
| Copper | 1 | 0.55 |
| Titanium | 5.06 | 0.369 |

Figure 4:
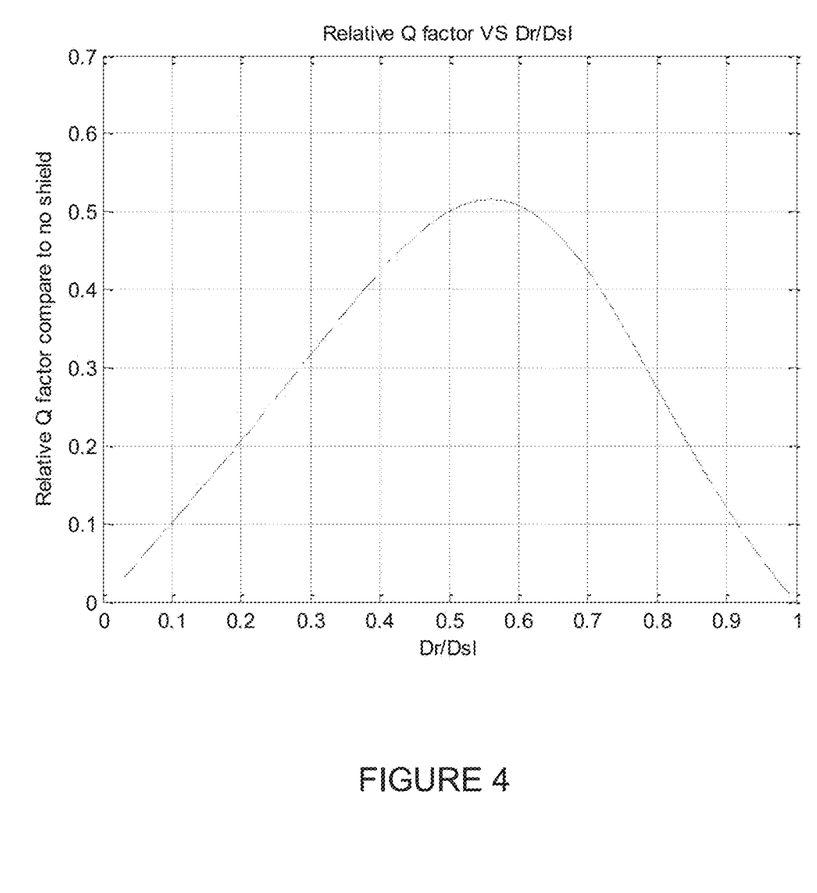
FIG. 4 is a graph of a relative quality factor (Q factor) of a resonator versus the ratio of the resonator diameter ($D_r$) and the ratio of an outer sleeve diameter ($D_{sl}$) of an NMR pipe in accordance with one embodiment.

As shown in FIG. 4, when the shielding layer 46 and the resonator 42 are made of the same material (e.g. copper), the ratio of the diameter of the resonator coil ($D_R$) and the diameter of the shielding layer ($D_{SL}$) are preferably optimized at about 0.55, which causes the resonator coil to have the highest Q factor for the limited volume available within the outer layer 44. Furthermore, it can also be seen in FIG. 4 that an increase in the resonator coil diameter in order to fit it into the available inner diameter of the outside conducting pipe, i.e. where the $D_R/D_{SL}$ ratio approaches 1, leads to a drastic drop in the Q value.

Interior of the shielding layer 46 is the gap or insulating layer 48 that creates a non-conductive space between the shielding layer and the innermost core layer 50 for optimum Q as shown in FIG. 4. The gap layer is filled with material in order to prevent flow of fluid on the outside of the resonator coil and to prevent the coil from mechanical wear. With this configuration, the gap layer also transfers the high pressure forces of a fluid sample within the pipe to the outer layer 44. Resins, as known to those skilled in the art, are suitable materials for the gap layer, as they are non-conductive and have sufficient mechanical strength. Another suitable material is polyetheretherketone (PEEK). The thickness of the gap layer 48 is defined by $(D_r - D_{sl})/2$.

The inner core layer 50 is a hollow cylinder for containing the fluid sample 52 within the inner core volume such that the fluid sample is in contact with the inner surfaces of the inner core layer. The inner core layer also provides support for the resonator 42 that is contained within the insulating layer. A suitable material for the core layer is polyetheretherketone (PEEK) which is non-metallic and has a high resistance to corrosion caused by a typical chemical environment of the fluid sample. Another suitable material for the inner core layer is Teflon®. It is preferable that the inner core layer 50 be made as thin as possible in order to maximize the sample volume; however the thinness of the inner core layer is restricted by factors including the abrasiveness of the fluids.

The resonator 42 is preferably a standard solenoid coil wrapped around the core layer that is immersed and contained within the gap layer 48. Preferably, the length L of the coil along the tube is at least twice the diameter of the coil which increases the homogenous radiofrequency (RF) field area inside the coil. It is preferable to use multiple wires connected in parallel which increases both the RF field homogeneity and the Q value of the coil.

Method for Determining Fluid Content

Methods for determining the properties of fluids, including the oil, water, solvent and gas content, at oil and gas well heads using NMR relaxometry are described. The measurements are taken in either stationary or flowing modes for the fluid.

Measurement of Oil and Water Content in a Stationary Fluid

Figure 5:
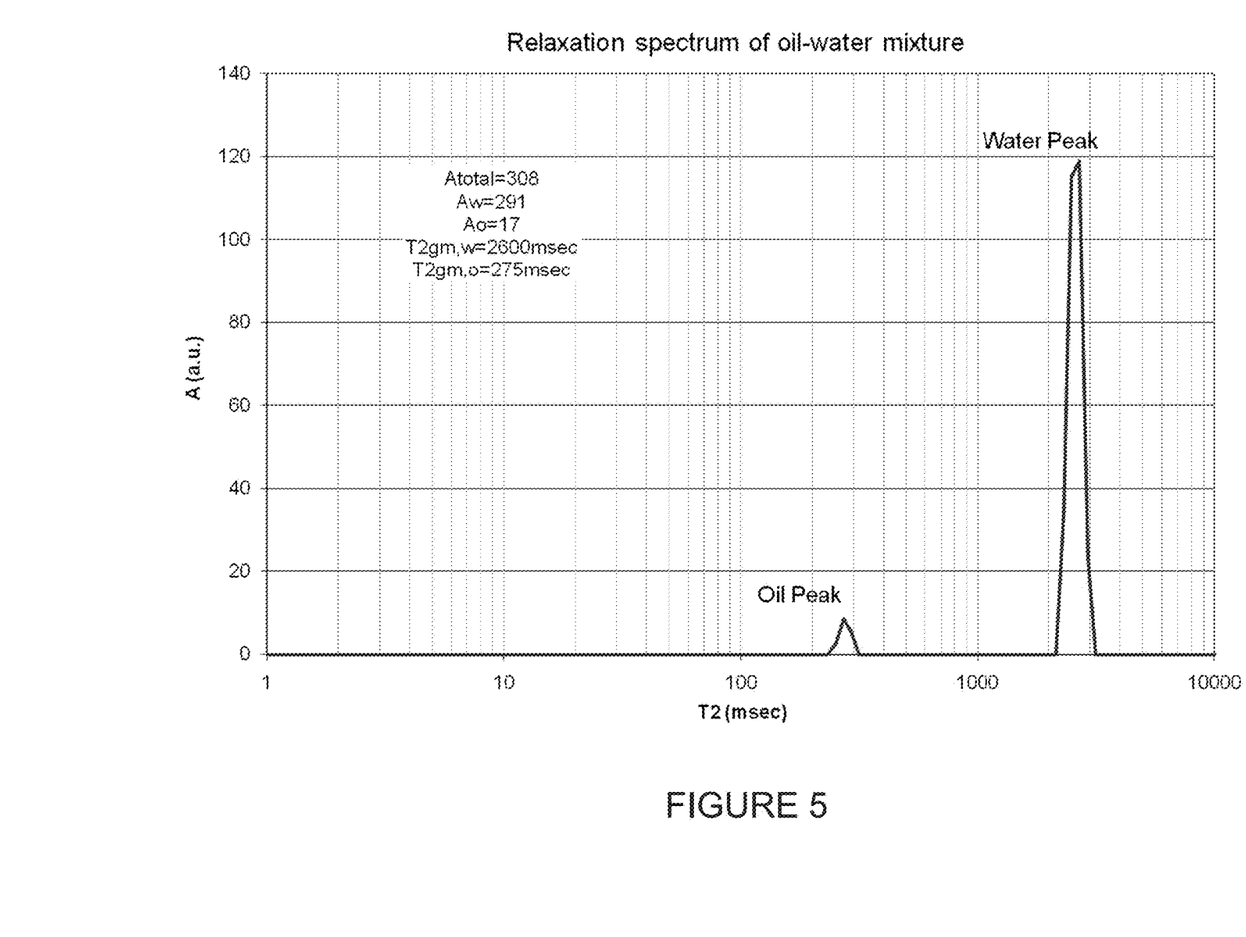
FIG. 5 is a graph of a relaxation spectrum of an oil and water mixture in accordance with one embodiment.

To determine the oil and water content of a stationary fluid in a pipe running through an NMR meter, a heavy oil (bitumen) and water signal are separated in the NMR T2 relaxation spectrum. The two measurements can be taken independently of each other. The graph in FIG. 5 illustrates a typical observed separation of oil and water peaks.

Assuming that the pipe is totally and uniformly filled with a mixture of oil and water (or radial sensitivity of NMR is uniform), the signal from water is proportional to the amount of water in the mixture in the following sense:

$$A_w(T,P) = \int AI_w(T,P,\bar{r}) \rho_w(T,P) S_w(\bar{r}) d^3\bar{r} \quad (1)$$

where T is temperature, P is pressure, $\bar{r}$ is a vector representing integration element position, $A_w(T, P)$ is total water amplitude, $AI_w(T, P, \bar{r})$ is water (mass) amplitude index, $\rho_w(T, P)$ is water density, and $S_w(\bar{r})$ is current water saturation (portion of the fluid volume element occupied by water). In the case of the uniform fluids distribution only $AI_w(T, P, \bar{r})$ is spatially dependent, then:

$$A_w(T,P) = \rho_w(T,P) S_w \int AI_w(T,P,\bar{r}) d^3\bar{r} \quad (2)$$

The amount of oil in the fluid can be determined by replacing water with oil in the above formulae.

Calibration of the system is performed with the pipe filled with water only based on the following:

$$A_{w,100\%}(T,P) = \rho_w(T,P) \int AI_w(T,P,\bar{r}) d^3\bar{r} \quad (3)$$

Water cut (volumetric) ($S_W$) within a cross-section of the pipe inside the magnetic field can be obtained according to the following relation:

$$S_w = \frac{A_w(T, P)}{A_{w,100\%}(T, P)} \quad (4)$$

As $S_w + S_o = 1$, then $S_o = 1 - S_w$.

Volumetric water cut can be converted into the mass water cut ($WC_m$) by the following:

$$WC_m = \frac{S_w \rho_w(T, P)}{S_w \rho_w(T, P) + S_o \rho_0(T, P)} \quad (5)$$

Radial variations of $AI_w(T, P, \bar{r})$ in a properly designed NMR relaxometer can be as low as 1% and even less. However, within the length of the measured volume of the pipe inhomogeneities of the magnetic field will exist. There may also be variations in water saturation along the length of the pipe if the system is flowing. To account for these variations, the above formulae become:

$$A_w(T,P) = \int AI_w(T,P,z) \rho_w(T,P) (\int S_w(x,y,z) dx \times dy) dz \quad (6)$$

or $$A_w(T,P) = \int AI_w(T,P,z) \rho_w(T,P) \bar{S}_w(z) dz \quad (7)$$

where $\bar{S}_w(z) = (\int S_w(x,y,z) dx \times dy)$ is water saturation averaged over the pipe cross-section. With the flow in the pipe stationary and settled, this value does not depend on z and again:

$$A_w(T, P) = \rho_w(T, P) \bar{S}_w \int AI_w(T, P, z) dz \quad (8)$$

$$A_{w,100\%}(T, P) = \rho_w(T, P) \int AI_w(T, P, z) dz \quad (9)$$

$$\bar{S}_w = \frac{A_w(T, P)}{A_{w,100\%}(T, P)} \quad (10)$$

Measurement of Water and Gas Content in a Stationary Fluid

The last set of formulae can be applied to any two phase system present in the pipe. If it is known that the only phases present are gas and water then the above formulae still give the volumetric water saturation $S_w$ and volumetric gas saturation $S_g = 1 - S_w$. The mass gas-water ratio (GWR) can be established based on the equation of state of gas at the known pressure and temperature:

$$GWR = \frac{S_g \rho_g(T, P)}{S_w \rho_w(T, P)} \quad (11)$$

Measurement of Oil and Gas Content in a Stationary Fluid

The above water-gas measurement procedure is directly transferable to oil-gas flows.

$$A_o(T, P) = \rho_o(T, P)\bar{S}_o \int AI_o(T, P, z)dz$$

$$A_{o,100\%}(T, P) = \rho_o(T, P) \int AI_o(T, P, z)dz$$

$$\bar{S}_o = \frac{A_o(T, P)}{A_{o,100\%}(T, P)}$$

It should be understood that the measurement of the value:

$$A_{o,100\%}(T,P) = \rho_o(T,P) \int AI_o(T,P,z)dz$$

for oil will require a sufficient amount of oil in order to perform a calibration procedure. As oil properties are subject to more variation than water properties, calibration procedures must occur more frequently.

Measurement of Oil, Water and Gas Content in a Stationary Fluid

In order to determine the oil, water and gas content of the flow, the measurements of oil and water signals in an appropriate range of relaxation times can be applied as follows:

$$A_w(T,P) = \rho_w(T,P)\bar{S}_w \int AI_w(T,P,z)dz \quad \text{(Water)}$$

$$A_o(T,P) = \rho_o(T,P)\bar{S}_o \int AI_o(T,P,z)dz \quad \text{(Oil)}$$

$$A_{o,100\%}(T,P) = \rho_o(T,P) \int AI_o(T,P,z)dz \quad \text{(Pure Oil)}$$

$$A_{w,100\%}(T,P) = \rho_w(T,P) \int AI_w(T,P,z)dz \quad \text{(Pure Water)}$$

Integration above is performed over the oil or water peak accordingly (see FIG. 5). Typically, the entire oil spectrum is below 300 ms and the water spectrum is above this threshold.

$$S_w = \frac{A_w(T, P)}{A_{w,100\%}(T, P)} \quad (12)$$

$$S_o = \frac{A_o(T, P)}{A_{o,100\%}(T, P)} \quad (13)$$

$$S_g = 1 - S_w - S_o \quad (14)$$

Conversion of volume fractions into mass fractions can be performed as above with the use of PVT properties of each phase.

The instrument must be calibrated by filling the pipe with water (equations (3)/(9)) or oil (for oil equivalent of equation (9)). $A_{w,100\%}(T, P)$, $A_{o,100\%}(T, P)$ for the full range of operating temperatures and pressures is done prior to installation. If the produced water and oil do not chemically change during production, then this calibration is sufficient. However, in order to account for noise and changes in production fluid properties, bi-annual calibrations are preferable. If the instrument is move to a different production location recalibration is preferable.

Calibration Procedure for Oil

In order to minimize the frequency of performing the oil calibration procedure, the following alternate oil calibration procedure can be performed.

For three phase measurements, the $A_{o,100\%}(T, P)$ may be difficult to obtain. If the system can be operated in two-phase mode without gas then the following calibration can be made. The system is run in two-phase mode (no gas) and measurements are taken. For the flow without a gas phase $S_o + S_w = 1$. With the use of previous relations this can be represented as $$\frac{A_w(T, P)}{A_{w,100\%}(T, P)} + \frac{A_o(T, P)}{A_{o,100\%}(T, P)} = 1 \quad (15)$$

$A_{w,100\%}(T, P)$ is a relatively simple function to measure in the laboratory. Then the following equation will be applicable:

$$A_{o,100\%}(T, P) = A_{w,100\%}(T, P) \frac{A_o(T, P)}{A_{w,100\%}(T, P) - A_w(T, P)} \quad (16)$$

The above relation allows for the extraction of the unknown function $A_{o,100\%}(T,P)$ that can be used in three phase measurements later.

Measurement of Oil and Water Content in a Continuous Flow

In the past, the sample generally has to be still (little or no movement) in order to determine the proportions of various components of the sample (e.g. when using NMR as a water-cut meter to determine the proportion of water in a sample). To create a stationary sample, extra cost may be needed to take the samples from main flowing stream. For example, a by-pass may be built for the main flowing stream for taking NMR measurements. When sampling from main flowing stream, the intensity of the signal from flowing fluid drops. As a result, the time per each measurement has to be increased so that the desired accuracy of measurement is achieved. Depending on the flow parameters this time increase can be from several minutes to tens of minutes.

The water-oil measurement procedure described in the previous section may be adapted for continuous oil-water flow if, for example, only the oil component (the fast-relaxing component in this case) is tracked in velocities that allow collection of the oil relaxation signal without counting for the water relaxation signal.

$$A_o(T, P) = \rho_o(T, P)\bar{S}_o \int AI_o(T, P, z)dz$$

$$A_{o,100\%}(T, P) = \rho_o(T, P) \int AI_o(T, P, z)dz$$

$$S_o = \frac{A_o(T, P)}{A_{o,100\%}(T, P)}$$

It should be understood that the measurement of the value:

$$A_{o,100\%}(T,P) = \rho_o(T,P) \int AI_o(T,P,z)dz$$

for oil will require a sufficient amount of oil in order to perform calibration procedure. As oil properties are subject to more variation than water properties this may mean performing calibration procedures more frequently.

It will be appreciated that this measurement procedure may be used for any two-component fluid mixture where the relaxation times of the components are sufficiently different (e.g. with relaxation ranges which do not substantially overlap—some overlap may be accommodated but any overlap may affect the accuracy of the determination). The measurement period may correspond to the relaxation time of the fast-relaxing component. The measurement period may be less than the relaxation time range of the slower-relaxing component. For example, in one water-oil example, the $T_{2gm}$ value for bitumen is 10-100 ms and the $T_{2gm}$ for water is, for example, several hundred milliseconds. In this case, the measurement period would be, for example, 100 ms (or less than several hundred milliseconds). That is, the measurement period may correspond to a time greater than the relaxation time range of the fast-relaxing component and less than the relaxation time range of the slow-relaxing component.

If the replacement of measuring mixture is much smaller than the NMR sweet spot length during the measurement period, the fast-relaxing component (e.g. bitumen) may be measured accurately. That is, because the replacement of the measuring mixture is small, the volume of sample in the sweet spot is largely composed of material which has been activated by the NMR signal. The replacement measuring mixture may be considered to be the volume of sample which is introduced into the sweet spot during the measurement period which has not been activated by the NMR signal.

For typical fluid flow speeds (e.g. up to 3 m/s) the fluids with relaxation times of less than 10 ms can be measured accurately as their NMR signal is substantially the same as it would be if the fluid were stationary.

In two-component mixtures (e.g. where there is no gas), the proportion of slow-relaxing component can be calculated by subtracting the proportion of the fast-relaxing component from 1. In the case of an water-oil sample, the water signal is calculated as: $S_w=1-S_o$.

Advantages of this method include that the measurement does not require subsampling (i.e. subsampling involves doing measurements on a portion of the fluid that was produced). In addition, by being performed frequently (e.g. every few minutes) the properties of the flow can be more effectively averaged, thereby producing more reliable data. It will be appreciated that, because the measurement may be obtained on a shorter time scale by only measuring the fast-relaxing component, the measurement may be repeated more frequently.

For mixtures with more than two components, this technique may be applied by setting the measurement period such that all but the slowest relaxing component is measured. The slowest relaxing component may then be determined by subtracting the proportions of the measured components from 1.

Flow Rate/Speed Considerations

In one embodiment, the NMR apparatus has a coil length of 20 cm. The sweet spot length of the coil may be ¾ of the coil length (=¾ of 20 cm=15 cm). In this case, the two-component mixture comprises heavy bitumen and water. For heavy bitumen, the typical $T_{2gm}$ value may be around 1 ms to 100 ms depending on the temperature of the sample. For this technology, the high-temperature (e.g. 150° C.-200° C.) $T_{2gm}$ value will be around 100 ms. In this case, the measurement period for measuring the bitumen component is set to be 100 ms (i.e. corresponding to the upper limit of the relaxing time range). The apparatus may be configured to set the measurement period based on the temperature of the sample (e.g. as measured by a thermometer such as a thermocouple).

A measurement may comprise using one or more CPMG trains. Using multiple CPMG trains allow for averaging and increasing of the signal to noise ratio (SNR). The measurement period may correspond to the length of one CPMG train.

The upper limit on the speed of the fluid, $s_l$, may be related to the maximum proportion of replacement of the sample, p, during the measurement period, $t_m$, of the measurement, and on the length of the sweet spot, $l_{ss}$, as follows:

$$s_l = \frac{pl_{ss}}{t_m}$$

The maximum proportion of replacement of the sample, p, may be considered an upper limit on how much the sample may be replaced during the measurement period whilst not significantly affecting the measurement accuracy. In this case, the maximum proportion of replacement of the sample, p, during the measurement period may be ⅓. In this case, signal intensity is proportional to the non-replaced portion of the sample averaged over the measurement period, i.e. (1-0.5*p), assuming it did not relax during this period too much. Noise level does not change noticeably with p. So, the signal-to-noise ratio (SNR) is proportional to (1-0.5*p). For p=⅓, the SNR drops by ⅙ or ~17%.]. Therefore, in this case, the upper limit on the speed of the fluid flow is:

$$s_l = \frac{pl_{ss}}{t_m} = \frac{\frac{1}{3} \times 0.15 \text{ m}}{0.1 \text{ s}} = 0.5 \text{ m/s}$$

For bitumen-water samples where the temperature is lower, the upper limit on the speed may be higher. For example, at 80° C. the typical $T_{2gm}$ of bitumen is less than 10 ms. For this scenario, the measurement period will be 10 ms, and the corresponding upper speed limitation on the sample flow will be 5 m/s.

It will be appreciated that some embodiments may use different values for the maximum replacement sample proportion (e.g. less than 0.1, less than 0.2, less than 0.3, less than 0.4).

Some embodiments may have a flow rate monitor configured to measure the flow rate of the sample, $s_m$. In such embodiments, the replacement sample proportion may be calculated from the flow rate as:

$$p = \frac{t_m s_m}{l_{ss}}$$

From this calculated proportion, some embodiments may be configured to compensate for the replacement of the sample within the duration of the experiment. For example, the quantity of the fast relaxing component may be scaled by the proportion of material replaced throughout the duration of the measurement. That is, compensation may be related to the above replacement factor, p, and can be introduced in the currently available $T_2$ spectrum reconstruction techniques. The apparatus may be configured to control the flow speed of the sample based on the measurement period (e.g. by expanding or contracting the cross-section of the pipe in order to control the speed of the sample flow whilst maintaining the same volumetric flow rate through the pipe, or by having a by-pass pipe).

Method of Characterizing Flowing Fluid

A two-component measurement may be carried out as follows:

First, the pipe is filled with a two-component sample (e.g. of oil and water), where the proportion of the fast relaxing component is known (e.g. $S_{frc}=S_o=\frac{1}{3}$ oil). Then, a stationary measurement (little or no flow, or $s_m=0$ m/s) of this known sample is taken to get the amplitude of the oil, $A_{0.33oil}$.

Secondly, the amplitude of oil for a full pipe of fast relaxing component is calculated: $A_{0.33oil}=A_{0.33oil}/S_{frc}$ (e.g. $A_{0.33oil}/(\frac{1}{3})$). It will be appreciated that these two steps may be replaced by a single step in which the pipe is completely filled with oil (i.e. as this would give the amplitude of oil for a full pipe directly). It will be appreciated that in some situations, the composition of the oil may be known (e.g. when only the ratio of oil and water is not known) and so, the calibration stage may be omitted as the oil signal may be calculated from the known composition.

Thirdly, a measurement of a sample (e.g. with unknown proportions of fast and slow relaxing components) is taken whilst it is moving at a speed of $s_m$. This measurement gives an amplitude corresponding to the quantity of fast-relaxing component of $A_m$.

Fourthly, the sample of the proportion of fast-relaxing component is calculated to compensate for the speed of the sample flow using a sample flow rate speed factor, $V(s_m)$. That is, the fast relaxing component cut, $S_{frc}=A_m/V(s_m)$.

Figure 7:
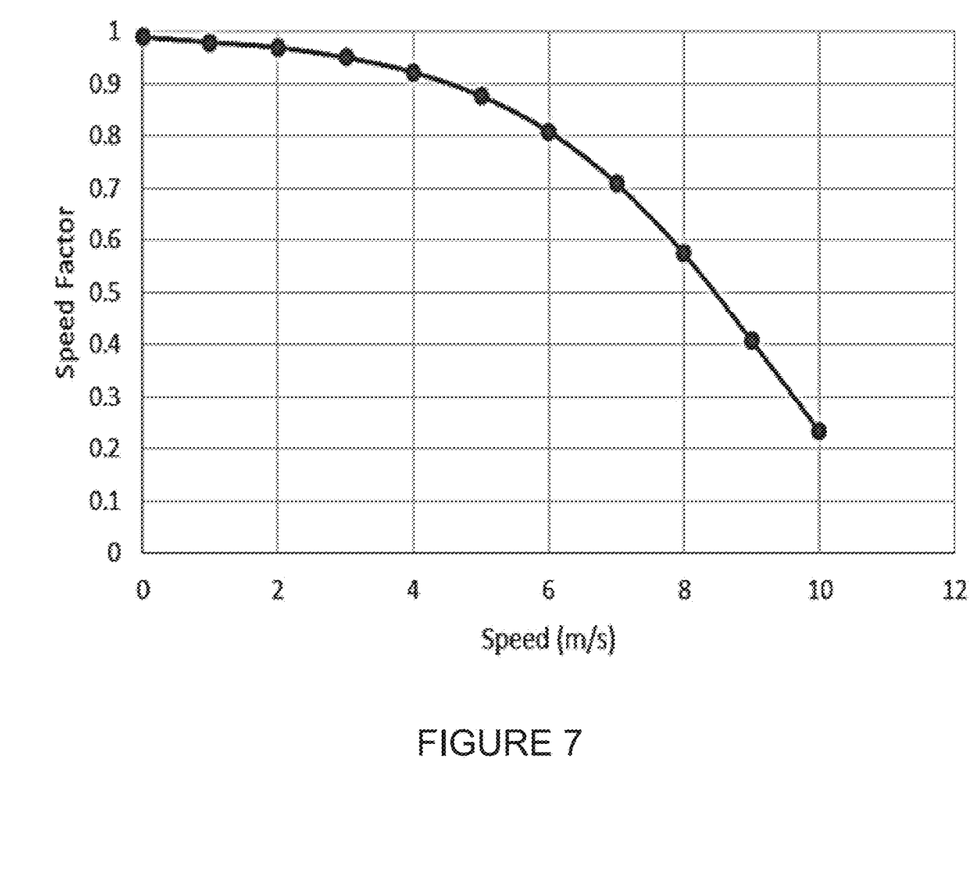
FIG. 7 is a graph of a speed factor which is used to compensate for the speed of a flowing sample.

The speed-factor is a function of speed, $s_m$, and can be determined based on on-site calibration (e.g. after hardware and software are finalized-hardware may contribute through the sweet spot length and flow diameter characteristics; software may define the CPMG train duration). If the speed is lower than a limiting speed (e.g. the limiting speed may be the same as the upper limit on the speed of the fluid flow, $s_l$), the speed-factor is around 1.0 (and so a speed-factor may not be used as speed compensation may not be required). If the speed is greater than this limiting speed, the speed-factor may be used as described above. FIG. 7 shows how the speed-factor varies with sample speed for one embodiment.

The value of the limiting speed may be dependent on the $T_{2gm}$ value of the fast relaxing components for a given temperature (shorter $T_{2gm}$, higher limiting speed); and/or the coil length and/or the length of the homogeneous magnetic field length (sweet spot length) (longer length, higher limiting speed).

Fifthly, the proportion of slow-relaxing component (e.g. water) is calculated by subtracting the proportion of fast-relaxing component from 1.

In this way, the relative quantities of fast-relaxing and slow-relaxing components in a sample flow using nuclear magnetic resonance (NMR) relaxometry are measured by:

flowing a sample comprising at least two components through the pipe, the at least two components comprising a fast-relaxing component and a slow-relaxing component;

measuring a relaxation curve corresponding to at least one fast-relaxing component as the sample flows through the pipe;

calculating a proportion of fast-relaxing component in the flowing sample based on relaxation spectra obtained from the measured relaxation curve; and calculating a proportion of a slow-relaxing component in the flowing sample based on the calculated proportion of fast-relaxing component.

Field Trials/Examples

Figure 6:
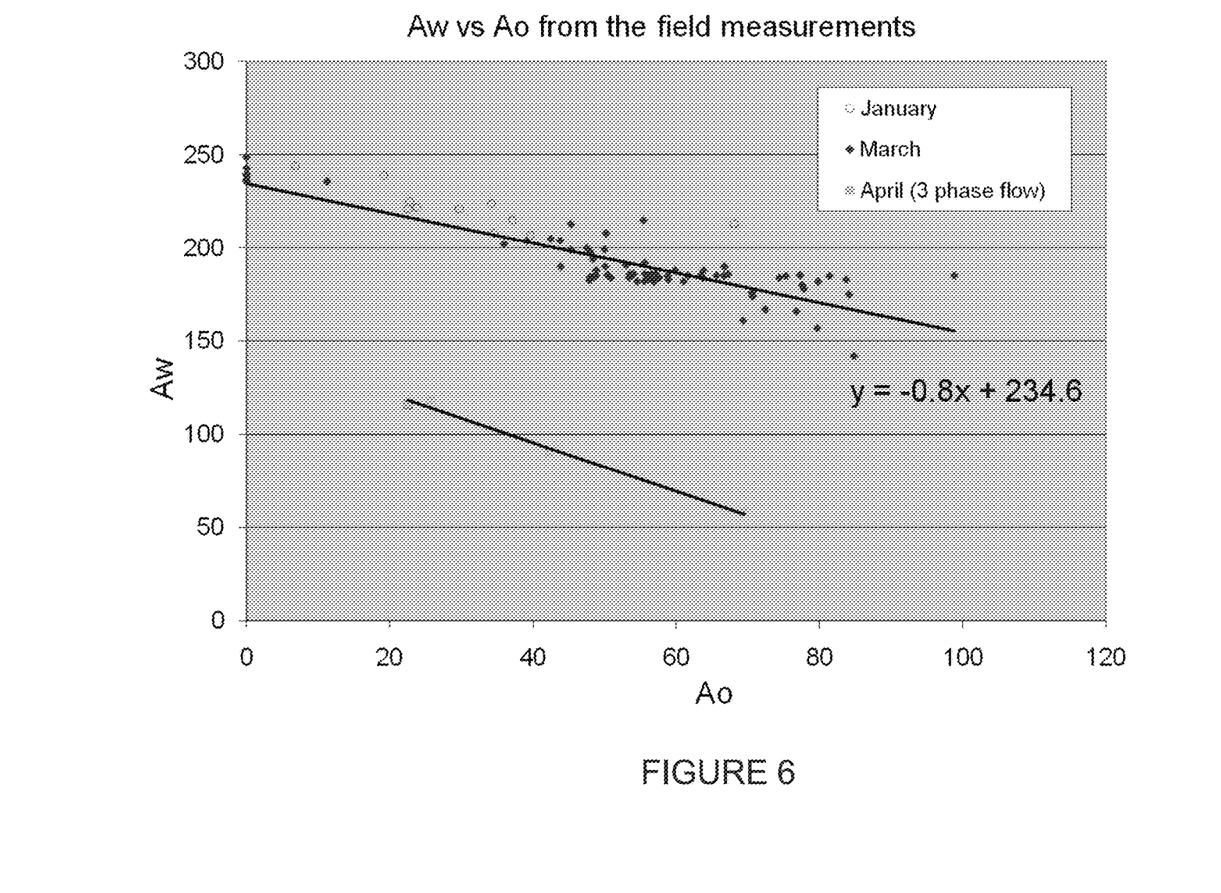
FIG. 6 is a graph of total water amplitude versus total oil amplitude for field measurements performed in accordance with one embodiment.

The graph in FIG. 6 presents field trial measurements for the NMR apparatus and method. As seen, the data fall closely on a straight line according to the relation as shown in Equation 16.

Table 2 shows a comparison of the NMR field data compared to Dean-Stark (lab) measurements for the same samples. The sample was split into two samples for the Dean-Stark measurements.

TABLE 2

A Comparison of NMR and Dean-Stark (DS) Water Cut (WC) Measurements For Four Samples.

| Sample # | WC from DS (%) | WC from NMR (%) |
|---|---|---|
| 1a | 82.85 | 82.4 |
| 1b | 82.77 | |
| 2a | 78.95 | 80.2 |
| 2b | 80.29 | |

Accordingly, the results show good correlation between the field measured and laboratory analysis samples.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A method of measuring the relative quantities of fast-relaxing and slow-relaxing components in a sample flow using nuclear magnetic resonance (NMR) relaxometry, comprising the steps of:
    flowing a sample comprising at least two components through the pipe, the at least two components comprising a fast-relaxing component and a slow-relaxing component;
    measuring a relaxation curve corresponding to at least one fast-relaxing component as the sample flows through the pipe, by applying an electromagnetic field to the sample and recording a signal response using an NMR coil;
    calculating, using a processor, a proportion of fast-relaxing component in the flowing sample based on relaxation spectra obtained from the measured relaxation curve; and
    calculating, using the processor, a proportion of a slow-relaxing component in the flowing sample based on the calculated proportion of fast-relaxing component; and
    enabling presentation of the calculated proportion of fast-relaxing and slow-relaxing components on a user interface.

2. The method of claim 1, wherein the at least one fast-relaxing component comprises oil.

3. The method of claim 1, wherein the at least one slow-relaxing component comprises water.

4. The method of claim 1, wherein the method comprises: calibrating the NMR pipe with a stationary sample comprising a known proportion of a fast-relaxing component.

5. The method of claim 1, wherein the calibration step comprises calibrating the NMR pipe with a pure sample of the fast-relaxing component.

6. The method of claim 1, wherein the fluid is flowing at a speed that allows collection of a fast-relaxing component relaxation signal without counting for a slow-relaxing component relaxation signal.

7. The method of claim 1, wherein the method comprises repeating one or more of the calibration steps over a selected temperature range.

8. The method of claim 1, wherein the proportion of the slow-relaxing component, $S_{src}$, is calculated as: $S_{src}=1-S_{frc}$, where $S_{frc}$ is the proportion of fast-relaxing component.

9. The method of claim 1, wherein the method comprises creating the relaxation spectra for the sample using a standard NNLS (non-negative least-squares) algorithm.

10. The method of claim 1, wherein mixture consists of two components.

11. The method of claim 1, wherein the method comprises:
   measuring the sample flow rate; and
   calculating a cut of a slow-relaxing component based on relaxation spectra obtained from the measured relaxation curves and on the measured flow rate.

12. The method of claim 1, wherein the measurement period corresponds to a time greater than the relaxation time range of the fast-relaxing component and slower than the relaxation time range of the slow-relaxation component.

13. The method of claim 1, wherein the method comprises:
   measuring the temperature of the sample; and
   setting a measurement period based on the measured temperature of the sample.

14. The method of claim 1, wherein the method comprises:
   measuring a relaxation curve corresponding to at least one fast-relaxing component during a measurement period; and
   controlling the flow rate of the sample based on the measurement period duration.

15. An NMR apparatus for measuring the relative quantities of fast-relaxing and slow-relaxing components in a sample flow using nuclear magnetic resonance (NMR) relaxometry, the NMR apparatus comprising:
   a pipe configured to receive a flowing sample comprising at least two components, the at least two components comprising a fast-relaxing component and a slow-relaxing component;
   NMR components configured to measure a relaxation curve corresponding to at least one fast-relaxing component of the flowing sample; and
   a processor configured to calculate a proportion of fast-relaxing component in the flowing sample based on relaxation spectra obtained from the measured relaxation curve; and to calculate a proportion of a slow-relaxing component in the flowing sample based on the calculated proportion of fast-relaxing component.

16. A method of measuring the relative quantities of components in a fluid using nuclear magnetic resonance (NMR) relaxometry in an NMR pressure tube or pipe, comprising the steps of:
   calibrating the NMR pressure tube or pipe with a pure oil sample by putting a pure oil sample within the NMR pressure tube and applying an electromagnetic field to the sample and recording a signal response using the NMR coil thereby providing a pure-oil calibration curve;
   introducing at least a two-component mixture into the NMR pressure tube or pipe, wherein the mixture comprises oil and water;
   measuring relaxation curves of a hydrogen signal by applying an electromagnetic field to the mixture and recording a response using the NMR coil;
   calculating water-cut using a processor based on relaxation spectra obtained from the measured relaxation curves; and
   enabling presentation of the calculated water-cut on a user interface.

17. An NMR apparatus for measuring the relative quantities of components in a fluid, the NMR apparatus comprising a electronic circuit having a processor and a NMR pressure tube, the NMR apparatus being configured to:
   calibrate the NMR pressure tube or pipe with a pure oil sample;
   introduce at least a two-component mixture into the NMR pressure tube or pipe, wherein the mixture comprises oil and water;
   measure relaxation curves of a hydrogen signal; and
   calculate water-cut based on relaxation spectra obtained from the measured relaxation curves.

* * * * *

UNITED STATES PATENT AND TRADEMARK OFFICE
CERTIFICATE OF CORRECTION

Page 1 of 1

PATENT NO.         : 10,371,653 B2
APPLICATION NO.    : 14/925509
DATED              : August 6, 2019
INVENTOR(S)        : Serguei I. Krioutchkov It is certified that error appears in the above-identified patent and that said Letters Patent is hereby corrected as shown below:

On the Title Page

Item [30], insert:
-- October 13, 2010 (CA) 2717541 --

Signed and Sealed this
First Day of October, 2019

Andrei Iancu
*Director of the United States Patent and Trademark Office*